United States Patent [19]

Massaro

[11] Patent Number: 5,141,877
[45] Date of Patent: Aug. 25, 1992

[54] METHOD FOR THE DETERMINATION OF THE PRESENCE OF FREE LIGHT CHAINS IN URINE

[75] Inventor: Leonardo Massaro, Paderno Dugnano, Italy

[73] Assignee: New Scientific Company S.p.A., Milan, Italy

[21] Appl. No.: 330,505

[22] Filed: Mar. 30, 1989

[30] Foreign Application Priority Data

Apr. 1, 1988 [IT] Italy ................. 20089 A/88

[51] Int. Cl.⁵ .......................... C01N 33/536
[52] U.S. Cl. .................. 436/536; 436/539; 436/501; 436/512
[58] Field of Search ............... 436/512, 517, 805, 536, 436/811, 501, 539

[56] References Cited

U.S. PATENT DOCUMENTS

| | | | |
|---|---|---|---|
| 4,211,530 | 7/1980 | Goverde et al. | 436/536 |
| 4,311,788 | 1/1982 | Heuck | 436/536 |
| 4,708,939 | 11/1987 | Siedel et al. | 436/13 |
| 4,720,465 | 1/1988 | Jensen et al. | 436/805 |
| 4,792,529 | 12/1988 | Rudick et al. | 436/811 |
| 4,843,021 | 6/1989 | Noguchi et al. | 436/533 |

OTHER PUBLICATIONS

Heino, J.; Rajamaki, A.; Irjalak, "Turbidimetric measurement of Bence-Jones proteins using antibodies against free light chains of immunoglobulins. An artifact caused by different polymeric forms of light chains", Scand J. Clin. Lab Invest. Apr. 1984, 44(2) pp. 173-176 see abstract Dialog A.N.=84196104.

*Primary Examiner*—David L. Lacey
*Assistant Examiner*—Thomas Daley
*Attorney, Agent, or Firm*—Finnegan, Henderson, Farabow, Garrett & Dunner

[57] ABSTRACT

A method for the determination of the presence of free light chains (Bence Jones protein) in a unconcentrated and undiluted urine sample is provided in which the sample is reacted with an anti-free light chain antiserum reagent, where the presence of the free light chains is revealed by increase in turbidity of the reacted sample. By comparison with the turbidity of calibrators having predetermined concentrations reacted with anti-free light chain antiserum, a quantitative analysis of the amount of free light chains in the urine sample can be determined. A kit for performance of the analysis, including anti-free light chain antiserum reagent, calibrator, and reagent without antiserum, is also provided.

6 Claims, No Drawings

METHOD FOR THE DETERMINATION OF THE PRESENCE OF FREE LIGHT CHAINS IN URINE

BACKGROUND OF THE INVENTION

It is known that an immunoglobulin is schematically made up of two heavy chains and two light chains. Determinations of the presence of the free light chains, also called Bence Jones proteins, in the urine is of great interest from the diagnostic viewpoint.

The free light chains are present in traces in the serum of normal subjects but are practically absent in the urine. The presence of said light chains in the urine is an indication of the existence of a pathological condition, particularly of immunological nature.

Actually, the presence of free light chains in urine presupposes their anomalous increase in the serum of the subject but, given their low molecular weight, free light chains pass through the glomerular filter and do not persist in the blood. It is therefore necessary to perform an indirect investigation, ascertaining their presence in the urine.

The presence of free light chains in the urine, which is the consequence of the increase thereof in the blood, is associated with immunological pathologies which can be summarized as (a) the presence of monoclonal free light chains, i.e. immunoproliferative illnesses such as multiple myeloma, micromolecular myeloma, Waldenstrom's macroglobulinemia, chronic lymphatic leukemia and primitive amyloidosis; and (b) the presence of polyclonal free light chains, i.e. hyperimmune illnesses such as systemic lupus erythematosus, acute rheumatoid arthritis and secondary amyloidosis.

Diagnostic methods based on ascertainment of free light chains in the urine are of great interest but at present are blocked by the difficultes of performance of such an investigation. At present, the most widely used method calls for electrophoretic analysis of the concentrated urine.

This technique necessarily requires concentration of the sample because of the relatively small percentage of free light chains in the organic liquid even with serious pathological conditions of the subject. Electrophoretic examination of the unconcentrated sample results in unacceptably low sensitivity and the resulting unreliability. The time necessary for concentration is added however to the time required for electrophoretic analysis with the obvious drawbacks. The analysis performed on the concentrated samples undoubtedly raises the reliability of the results without however achieving reasonable certainty. On the samples which prove suspect under electrophoresis it is therefore very advisable to perform immunofixation or immunoelectrophoretic tests, the laboriousness and cost of which are known, to achieve truly satisfactory levels of sensitivity and hence reliability of the analysis results.

SUMMARY OF THE INVENTION

The object of the invention is to propose a qualitative and quantitative ascertainment method for the presence of free light chains in urine which would be easy to perform in extremely short times with a high degree of sensitivity, especially in comparison with the times required in the analysis processes presently used.

In addition it is an object of the invention to make available to the user a complex of substances in kit form suitable for putting into practice the proposed diagnostic method.

DETAILED DESCRIPTION OF THE PREFERRED EMBODIMENTS

The invention is based on the observation that an antigen-antibody reaction is usable for determination of the presence of free light chains in the urine without prior concentration, leading to turbidity values which allow appraisal of the presence of such chains with significant qualitative and quantitative reliability. In particular the invention proposes a diagnostic method based on ascertainment of the concentration of light chains in the urine comprising the phases (a) centrifugation of the urine sample and separation of the overfloating, (b) addition to the sample of an anti free light chain antiserum reagent operating with an excess of antibodies, and (c) appraisal of turbidity of the reacted sample.

In particular if a quantitative appraisal is required the method calls for addition of the antiserum reagent to a calibration sample containing free light chains in a predetermined quantity to obtain calibration curves for the quantitative analysis procedure by turbidity comparison.

The anti-light chain antiserum is obtainable by any of the known procedures for the purpose, generally from an animal immunized with free light chains.

Two types of light chain are known, conventionally denominated kappa and lambda, which can be used for immunization of animals to obtain corresponding antiserums.

Such an antiserum reacts with all of the antigen sites of the light chain including those which can be defined as 'hidden', when the light chain is linked to the heavy chain. This antiserum then shows both the linked light chains and the free light chains.

It is possible to obtain an anti-free light chain antiserum by separating therefrom the antibodies directed against the antigenic sites not 'hidden' by the light chain; this can be achieved by reacting the anti-free light chain antiserum with whole immunglobulins and recovering the antibodies which have not reacted. Such an antiserum reacts only with kappa or lambda free light chains, respectively, and does not react with linked light chains.

To better clarify the characteristics of the method in accordance with the invention, a practical embodiment thereof is described below.

A kit of products necessary for performing the analysis in accordance with the invention typically includes the following components:

(a) Anti-free light chain antiserum reagent consisting of dilute antiserum, e.g. in concentrations of 20% anti-free kappa light chain antiserum, 20% anti-free lambda light chain antiserum, and 60% of a 4% solution of PEG 6000 in a physiological buffer solution (PBS) (phosphate buffer at pH 7.4) It is advantagaeous to add a preservative such as 0.1% Sodium Azide.

(b) Calibrators.

These can be used as positive controls of the qualitative procedure and as calibrators for the quantitative procedure.

The samples used come from patients with secretory micromolecular myeloma. In the absence of any reference method in the literature electrophoresis was performed on the urinary proteins, noting the presence of a large band subsequently typed with immunofixation as free kappa and lambda light chains accompanied by a barely visible band of albumin. The quantity of total proteins is therefore considered to practically coincide with the quantity of free light chains. The concentration of the total proteins was performed by the Bradford method. The samples are freeze-dried with addition of preservative (1% Sodium Azide) to be diluted with distilled water for use, then with PBS to plot the standard curve for the quantitative procedure.

(c) Reagent without antiserum. The composition of this reagent is the same as that of the antiserum reagent but without the latter and to be used in the control and calibration procedure as standard white.

The operating procedure for performance of the analysis in accordance with the invention can be summmarized as follows.

The reagents with and without antiserum are brought to surrounding temperature, filtering the volume of the former necessary for the analysis if it should not be limpid.

The reagent without antiserum is mixed in a test tube with the calibrator and the resulting reacted substance must be limpid.

Then the antiserum reagent is mixed with the calibrator and the reacted substance must be turbid.

If the readings are not those expected it is due to a procedural error or an anomaly of the reagents and these must therefore be discarded.

After centrifugation of the sample it is treated with antiserum reagent. Turbidity is a sign of the presence of kappa or lamda light chains or both.

The details of the procedures for performance of the antiserum-sample reaction are not given here as they are the usual ones followed in carrying out antigen-antibody reactions. It is clear that operation will be with an excess of the latter and, for doubtful or negative samples, an extra quantity of urine can be added to the reaction test tube, then appraising whether said addition modifies the turbidity appreciably.

For instrumental quantity-reading the calibration curve must be constructed repeating the analysis procedure with antiserum reagent on samples obtained from solutions in various percentages of calibrator in saline buffer solution.

For example turbidity values can be determined on 20, 40, 60, 80 and 100% calibrator solutions. It is thus possible to show on a Cartesian chart the concentrations of free light chains of the calibrator solutions on the basis of the optical density in comparison with the standard white, measuring with a suitable instrument such as the Mod. 336 Biotron Photometer or the Cobas Bio Analyser (Roche).

As mentioned above the concentration of free light chains in the calibrator presented as freeze-dried to be reconstituted by dilution in a predermined quantity of distilled water is known.

An alternative to the abovementioned procedure is possible using not a single kappa and lambda anti-free light chain antiserum reagent but two separate kappa and lambda anti-free light chain reagents respectively. In this manner there are obtained separate results of concentration of the two types of chains when desired for particular diagnostic or experimental requirements. Nothing else changes in the above-mentioned procedure. In this case it is advisable to prepare in advance kappa and lambda calibrators respectively for the checks preceding the sample analysis procedure and construction of the calibration curves for the quantitative analysis.

The results of the analysis were verified by performance of a conventional electrophoretic examination of the samples analysed in accordance with the invention, obtaining confirmation of the correctness of the results obtained by the latter. Samples which proved negative under conventional electrophoretic examination proved positive with a sample concentration of from 10 to 50 times depending on the practices of the different laboratories.

The singular and astonishing effectiveness of the method is demonstrated by the fact that a concentration of approximately 4 mg/dl of light chains was evaluated with it, demonstrating that the use in this specific field of the antigen-antibody reaction technique has led to satisfactory results for the problem of identificaton of free light chains in urine.

Practically the only limit to the method is its inability to distinguish between monoclonal and polyclonal light chains as is possible using electrophoretic analysis with immunofixation.

However, the positive nature of the analysis for only one of the two light chains, kappa or lamda, can be considered a reasonably certain sign of monoclonality of the chains present in the sample.

But this limitation is largely compensated for by the speed, reliability and simplicity of performance of the method in accordance with the invention compared with the one previously used for this purpose. Only on the samples which proved positive under analysis in accordance with the invention will it be required to perform further immunoelectrophoretic analyses or with immunofixation to determine the nature of the free light chains if desired.

On this point it should be noted that in this type of diagnostic analysis the positivity is to be considered, if not rare, certainly very infrequent statistically. It is thus very useful to have available the method in accordance with the invention which permits a first screening of the samples with very high sensitivity and reliability of the result because the examinations can be pursued further on the limited number of samples which proved positive on analysis.

I claim:

1. A method for the determination of the presence of free light chains in unconcentrated and undiluted samples of urine comprising the steps of (a) centrifuging the urine sample and separating the resulting supernatant, (b) adding to the supernatant an anti-light chain antiserum reagent in an amount sufficient to provide antibodies in excess, and (c) determining the turbidity of the reacted supernatant.

2. The method according to claim 1, wherein the sample is reacted successively with anti-free kappa and anti-free lambda light chain antisera.

3. The method according to claim 1, wherein the turbidity of the reacted sample is determined by comparison with the product of reaction of the antiserum reagent with a calibrator having a predetermined content of free light chains.

4. The method according to claim 3, wherein a calibration curve is constructed for the comparison by instrumentally determining the turbidity value of the reaction product of the antiserum reagent with samples made up of calibrator solutions in various concentrations.

5. The method according to claim 3, wherein the calibrator is obtained from the urine of patients with micromolecular myeloma.

6. The method according to claim 1, wherein the reagent is obtained by animal immunization with free light chains.

* * * * *